United States Patent [19]

Wachs

[11] Patent Number: 5,969,191
[45] Date of Patent: Oct. 19, 1999

[54] PRODUCTION OF FORMALDEHYDE FROM METHYL MERCAPTANS

[75] Inventor: Israel E. Wachs, Bridgewater, N.J.

[73] Assignee: Lehigh University, Bethlehem, Pa.

[21] Appl. No.: 08/944,867

[22] Filed: Oct. 6, 1997

Related U.S. Application Data

[60] Provisional application No. 60/029,031, Oct. 25, 1996.

[51] Int. Cl.$^6$ ..................................................... C07C 45/82
[52] U.S. Cl. .............................. 568/493; 568/21; 568/38; 568/69; 568/449
[58] Field of Search .................................. 568/21, 38, 69, 568/449, 470, 493

[56] References Cited

PUBLICATIONS

Silverman, The Organic Chemistry of Drug Design and Drug Action, pp. 19–21, 1992.
Turk, et al., "Ammonia Injection Enhances Capacity of Activated Carbon for Hydrogen Sulfide and Methyl Mercaptan," Enviro. Sci. Technol., vol. 23, No. 10, 1242–1245, 1989.
Weigand, et al., "The Local Structure of Absorbed methyl Thiolate: The Reactions of Methanethiol on Mo(110)," Surface Science, vol. 279, 105–112, 1992.
Bol and Friend, "The Effects of Oxygen on Selectivity: The Reactions of 2–Propanethiolate on Oxygen–Covered Rh(111)," J. Am. Chem. Soc., vol. 117, 5351–5358, 1995.
Bosch, et al., "Formation and Control of Nitrogen Oxides," Catalysis Today, vol. 2, No. 4, 369–379, 1988.
Busca, et al., "Mechanism of Selective Methanol Oxidation Over Vanadium Oxide–Titanium Oxide Catalysts: A FT–IR and Flow Reactor Study," J. Phys. Chem., vol. 91, 5263–5269, 1997.
Jehng, et al., "Surface Modified Niobium Oxide Catalyst: Synthesis, Characterization, and Catalysis, Applied Catalysis A," vol. 83, 179–200, 1992.
Kim and Wachs, "Surface Chemistry of Supported Chromium Oxide Catalyst," Journal of Catalysis, vol. 142, 166–171, 1993.
Jehng and Wachs, "Modecular Design of Supported Niobium Oxide Catalysts," Catalysis Today, vol. 16, 417–426, 1993.
Kim and Wachs, "Surface Rhenium Oxide–Support Interaction for Supported Re$_2$O$_7$ Catalysts," Journal of Catalysis, vol. 141, 419–429, 1993.
Deo, et al., "Physical and Chemical Characterization of Surface Vanadium Oxide Supported on Titania: Influence of Titania Phase (Anatase, Brookite and B)," Applied Catalysis A, vol. 91, 27–42, 1992.
Deo and Wachs, "Reactivity of Supported Vanadium Oxide Catalysts: The Partial Oxidation of Methanol," Journal of Catalysis, vol. 146, 323–334, 1994.
Deo and Wachs, "Effect of Additives on the Structure and Reactivity of the Surface Vanadium Oxide Phase in V$_2$O$_5$/TiO$_2$ Catalysts," vol. 146, 335–345, 1994.
Jehng, et al., "Surface Chemistry of Silica–Titania–Supported Chromium Oxide Catalysts," J. Chem Soc. Faraday Trans., vol. 91(5), 953–961, 1995.
Biaker, et al., "Molecular Structures and Reactivity of Supported Molybdenum Oxide Catalysts," vol. 146, 268–277, 1994.
Banares, et al., "Molybdena on Silica Catalysts: Role of Preparation Methods of the Structure–Selectivity Properties for the Oxidation of Methanol," Journal of Catalysis, vol. 150,407–420, 1994.
Jehng and Wachs, "The Molecular Structures and Reactivity of V$_2$O$_3$/TiO$_2$/SiO$_2$ Catalysts," Catalyst Letters, vol. 13, 9–20, 1992.
Hardcastle, et al., "Determination of Molybdenum–Oxygen Bond Distances and Bond Orders by Ramon Spectroscopy," J. Raman Spectroscopy, 21, 683–691, 1990.
Hardcastle, et al., Determination of Vanadium–Oxygen Bond Distances and Bond Orders by Raman Spectroscopy, J. Physical Chemistry, 95(13) 5031–5041, 1991.
Hardcastle, "Determination of the Molecular Structures of Tungstates by Raman Spectroscopy," J. Raman Spectroscopy, 26,397–405, 1995.
Weckhuysen, et al.,"Raman Spectroscopy of Supported Chromium Oxide Catalysts Determination of Chromium–Oxygen Bond Distances and Bond Orders," J. Chem. Soc. Faraday Trans., 92(11), 1969–1973, 1996.
Hardcastle, et al., "Determination of Noibium–Oxygen Bond Distances and Bond Orders by Raman Spectroscopy," Solid State Ionics, 45, 201–213, 1991.
Chemical Abstracts, 089(17), Abstr. No. 146366, "Possible Utilization of Dimethyl Ether", 1978.
Chemical Abstracts, 114(8), Abstr. No. 114(8), Abstr. No. 066367, "Photooxidation of Dimethyl Sulfide and Dimethy Disulfide. II:L Mechanism Evaluation", 1991.
Yin, et al., "Photooxidation of Dimethyl Sulfide and Dimethyl Disulfide. II: Mechanism Evaluation," J. Atmos. Chem., vol. 11, No. 4, 365–399, Cal. Inst. Tech., Dept Of Chem. Eng., Pasadena, 1990.
Mater. Vses. Konf., "Probl. Povysh. Urovnya Ispol'Z. Vtorichnykh Mater. Resur. Khim. Prom–Sti.," (38YXAG); 76, 105–111, Lenigr. Tekh. Inst., Lenigrad. USSR.

*Primary Examiner*—Shailendra Kumar
*Assistant Examiner*—S. Padmanabhan
*Attorney, Agent, or Firm*—Banner & Witcoff, Ltd.

[57] ABSTRACT

A method wherein a gas stream containing a methyl mercaptan is passed in contact with a catalyst comprising a supported metal oxide or a bulk metal oxide in the presence of an oxidizing agent and for a time sufficient to convert at least a portion of the methyl mercaptan to formaldehyde (CH$_2$O) and sulfur dioxide (SO$_2$)

20 Claims, 3 Drawing Sheets

PRODUCTION OF FORMALDEHYDE FROM METHYL MERCAPTANS

This application claims the benefit under 35 U.S.C. 119 (e)(1) of prior filed provisional application 60/029,031 filed Oct. 25, 1996.

BACKGROUND OF THE INVENTION

1. Field of the Invention

This invention broadly relates to a process for producing formaldehyde from methyl mercaptans, and especially formaldehyde from methanethiol. More particularly, this invention provides a method wherein a gas stream containing a methyl mercaptan is passed in contact with a catalyst comprising certain supported metal oxides or certain bulk metal oxides in the presence of an oxidizing agent and for a time sufficient to convert at least a portion of the methyl mercaptan to formaldehyde ($CH_2O$) and sulfur dioxide ($SO_2$).

2. Description of Related Art

Methyl mercaptans, such as methanethiol ($CH_3SH$), dimethyl sulfide ($CH_3SCH_3$) and dimethyl disulfide ($CH_3SSCH_3$), are found as impurities or produced as a generally undesirable by-product in a wide variety of industrial gas streams. These reduced sulfur compounds are exceedingly malodorous (detectable at parts per billion [ppb] levels), are extremely hazardous, and often are considered a pollutant. It is expected that their emission will be subject to more restrictive regulation in the future.

Noncatalytic gas phase oxidation of such reduced sulfur compounds produces primarily sulfur oxide and carbon oxide products. A. Turk et aL, *Envir. Sci. Technol* 23:1242–1245 (1989). Investigators have observed that oxidation in the presence of single-crystal metal surfaces (Mo, Ni, Fe, Cu) results in the formation of methane and ethane, nonselective decomposition to atomic carbon, gaseous hydrogen and the deposition of atomic sulfur on the metal surface via a stoichiometric reaction (See Wiegand et al., *Surface Science*, 279(1992): 105–112). Oxidation of higher mercaptans, e.g., propanethiol on oxygen-covered single-crystal metal surfaces (Rh), produced acetone via a stoichiometric reaction at low selectivity and accompanied by sulfur deposition on the metal surface (See Bol et al., *J Am. Chem. Soc.*, 117(1995): 5351–5258). The deposition of sulfur on the metal surface obviously precludes continuous operation.

Catalysts comprising a two-dimensional metal oxide overlayer on titania and 10 silica supports, e.g., vanadia on titania, have been used for catalytically reducing nitrogen oxides ($NO_x$) by ammonia to $N_2$ and $H_2O$ in the presence of sulfur oxides. Bosch et al, *Catal. Today* 2:369 et seq. (1988). Thus, such catalysts are known to be resistant to poisoning by sulfur oxides. It also is known that such catalysts, as well as certain bulk metal oxides catalysts, can be used to oxidize methanol to formaldehyde selectively. Busca et al, *J Phys. Chem.* 91:5263 et seq. (1987). Applicant now has made the discovery that these catalysts also can be used to oxidize methyl mercaptans selectively to formaldehyde in a continuous, heterogenous catalytic process without being poisoned by the reduced sulfur.

BRIEF DESCRIPTION OF THE INVENTION

Figure 1:
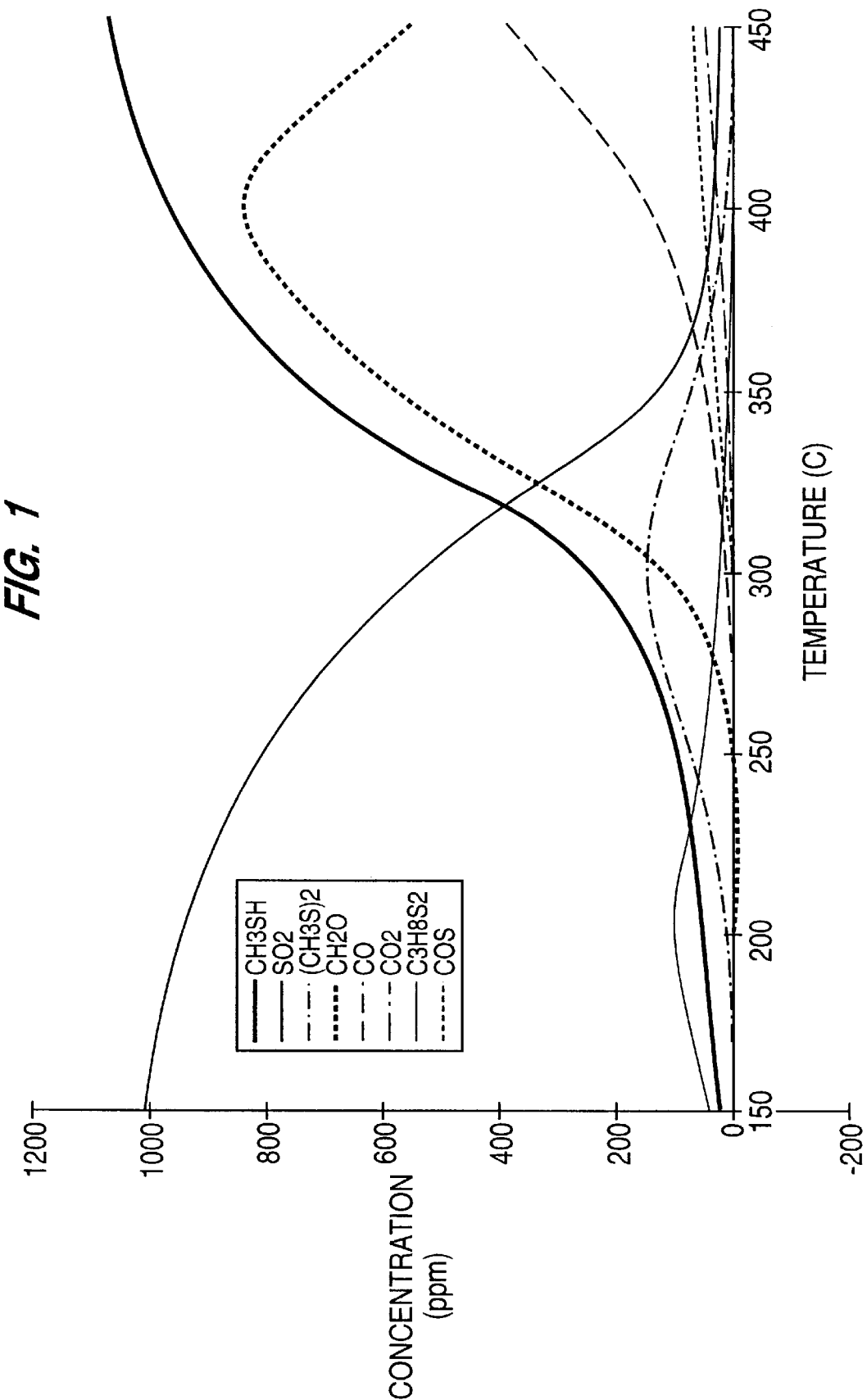
FIG. 1 illustrates the distribution of products (exit concentration of reactor) produced by oxidizing methanethiol over a vanadia on titania catalyst containing about 1% by weight vanadia over the temperature range of 150° to 450° C. Maximum selectivity for the conversion of methanethiol to formaldehyde was observed at a temperature of about 400° C. Starting at about 300° C., there was a significant conversion of methanethiol to formaldehyde.

The present invention is thus directed to a method for converting methyl mercaptans, such as methanethiol ($CH_3SH$), in a gaseous feed to formaldehyde and sulfur dioxide. The process involves flowing the gaseous stream containing methyl mercaptan in contact with a catalyst comprising a supported metal oxide or bulk metal oxide under oxidizing conditions for a time sufficient to convert at least a portion of the methyl mercaptan to formaldehyde and sulfur dioxide, and then recovering the formaldehyde as a product separate from the gas stream. In carrying out the process of the present invention, the metal oxide overlayer of the supported metal oxide is typically based on a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof and the support generally is selected from titania, silica, zirconia, alumina, ceria, magnesia, niobia, lanthanum oxide, tin oxide and mixtures thereof As a general rule, titanium (Ti), zirconium (Zr), niobium (Nb), tantalum (Ta) and tungsten (W) should not be used as the sole catalytic species with a silica support and the support and the supported metal should not be identical. In the alternative embodiment of the present invention, the process can be carried out using a bulk metal oxide catalyst wherein the bulk metal oxides, and especially bulk mixed metal oxides are based on molybdates (Mo), chromates (Cr), vanadates (V), rhenates (Re), titinates (Ti), niobates (Nb), tungstates (W) and mixtures thereof Catalysts based on molybdenum, chromium and vanadium are preferred.

The supported metal oxide and bulk metal oxide catalyst compositions useful for practicing the present invention are known in the prior art. The ability of these catalysts to convert methyl mercaptan to formaldehyde at a high selectivity was entirely unexpected.

In a preferred embodiment, the supported metal oxide is based on vanadium (V) and its admixture with one of molybdenum (Mo), tungsten (W), chromium (Cr), rhenium (Re), and manganese (Mn), supported on titania or silica. In the case of a vanadia on silica catalyst, an adjuvant selected from the group consisting of titanium, zirconium, cerium, tin, niobium and tantalium, should also be present to enhance catalytic activity. Vanadia on titania is particularly preferred as a metal oxide supported catalyst.

DETAILED DESCRIPTION OF THE INVENTION

As noted, the present invention is directed to a method for selectively converting methyl mercaptans, such as methanethiol ($CH_3SH$), in a gaseous feed to formaldehyde and sulfur dioxide. In accordance with the present invention, the gas stream containing the methyl mercaptan contacts the supported metal oxide or bulk metal oxide catalyst under oxidizing conditions at a temperature in the range of 200° to 700° C., preferably in the range of 300° to 600° C. and most often in the range of 325° to 500° C. The oxidizing agent can usually be oxygen or air. The contacting of the methyl mercaptan with the supported metal oxide catalyst or bulk metal oxide catalyst under an oxidizing atmosphere, e.g., in the presence of oxygen, and at an appropriate temperature, causes a selective conversion of the methyl mercaptan to formaldehyde. The oxidizable constituents of the gaseous feed stream generally will comprise at least about 0.01 mole %, preferably at least 0.1 mole % and most often about 1 mole % and higher of methyl mercaptan, although higher concentrations may be employed. The gas stream may include many other oxidizable or inert constituents. For illustrative purposes only, for example, other oxidizable components of the gas stream may include hydrogen sulfide, methane, and methanol. The gas stream may also include water. The gas stream contacts the catalyst at a temperature range of 200° to 700° C., preferably in the range of 300° to 600° C., and most often in the range of 325° to 500° C. A maximum temperature of 450° C. will often be suitable. The operating pressure for the catalytic reactor is not critical. Operation at atmospheric pressure has been found suitable.

To achieve high selectivity in the conversion of methyl mercaptan to formaldehyde it is important to maintain the flow rate of methyl mercaptan per unit mass of catalyst in the range of $10^{-2}$ to $10^4$ cubic centimeters (assessed under standard conditions of temperature and pressure (STP)) of methyl mercaptan per gram of active catalyst per minute (excluding inert ceramic components or other inert support material). Generally, higher reaction temperatures permit higher flow rates. Usually, the process can be operated at 0.1 to 100, cubic centimeters (STP) of methyl mercaptan per gram of catalyst per minute.

As used herein, the term "selectively" is intended to embrace the conversion of at least 1% of the methyl mercaptan, preferably at least 10% of the methyl mercaptan, more usually at least 50% of the methyl mercaptan and most preferably at least 70% of the methyl mercaptan which contacts the catalyst to formaldehyde. Selectivity, as that term is used herein, is determined by the percentage of formaldehyde in the mercaptan conversion products as a proportion of the carbon-containing mercaptan oxidation products.

The oxidation reaction is exothermic. As recognized by those skilled in the art a variety of reactor designs may be employed to accommodate the necessary mass and heat transfer processes for effective operation on a continuous basis. The reaction may be conducted at atmosphere pressure, and above or below atmospheric pressure.

Formaldehyde is the intended product and it can be recovered from the gaseous reaction products using anyone of a number of ways known to those skilled in the art.

In particular, as will be recognized by those skilled in the art, the gases leaving the reactor may contain unreacted starting products, including any inert gases that may have been added, as well as formaldehyde and water. The principal by-products that are formed include carbon monoxide, which may be accompanied by a small amount of carbon dioxide and sulfur dioxide. COS may also be a minor product. The sulfur dioxide can be recovered and converted to sulfuric acid by further oxidation.

The reaction mixture leaving the reactor is generally subject to further processing in a conventional manner. For example, the formaldehyde product can be separated in a washer, or by indirect cooling, or also by fractional cooling. For example, the washing can be performed with water, in which case a multi-stage washer or absorber can be used. An aqueous formaldehyde solution is obtained in this manner. From this solution commercial formaldehyde solutions can be prepared by distillation for immediate technical use. The formaldehyde also can be condensed out of the reaction gas together with the water that has formed. In this manner, concentrated formaldehyde solutions in common commercial form can be obtained. Other ways for isolating the formaldehyde product will be apparent to those skilled in this art.

For obtaining higher yields and selectivities in the conversion of methyl mercaptan to formaldehyde, it may be desirable to conduct the reaction such that only a partial reaction takes place in a single pass through the reactor. For example, the pressure, temperature, composition of the starting gas mixture, the amount of catalyst and/or the rate of flow can be varied to cause a partial conversion of the mercaptan feed. The reactor effluent gas remaining after separation of the formaldehyde can then be recycled into the reactor. It is desirable to add to this gas the amount of methyl mercaptan that has been consumed. In this manner, a continuous circulation can be achieved. If the gas is recirculated in this manner, the inert gases and the by-products, especially carbon monoxide, will concentrate in the recycled gas, and any excessive accumulation of these gases can be prevented by a continuous or discontinuous sidestream removal. It is also desirable to replace the removed exhaust gas with an equal amount of fresh gas.

The metal oxide of the supported metal oxide catalyst is accommodated in the support primarily as a two-dimensional metal oxide overlayer, with the oxide having a noncrystalline form. Thus, supported metal oxide catalysts useful in the process of this invention generally comprise a metal oxide substrate, such as titania, silica, zirconia, alumina, niobia, ceria, magnesia, lanthanum oxide and tin oxide, whose surface has been modified with a layer of an oxide of a metal or a mixture of metals as identified above (e.g., preferably vanadium, and mixtures containing vanadium) in an amount such that the catalyst exhibits properties different from the metal oxide substrate whose surface has not been modified. These catalysts also behave differently from bulk metal oxides of the metal oxide overlayer (e.g., bulk oxides of vanadium, and its mixtures). Consequently, in this embodiment of the invention, the metal oxide loading on the metal oxide support or substrate, e.g., titania, must be sufficient to modify the metal oxide surface, but not enough to result in a catalyst exhibiting properties of the bulk oxides of the metal oxide overlayer, e.g., a bulk oxide of vanadia. Thus, at least a portion of and preferably at least about 25 wt % of the metal oxide coating will be in a noncrystalline form. This will be accomplished if the metal oxide loading on the metal oxide support or substrate broadly ranges between about 0.5 to 35 wt % of the total catalyst weight.

A preferred metal oxide support is titania (titanium dioxide) which can be employed in the anatase form. For example, at least about 25 wt % (and generally from about 50 to about 100 wt %) of the titanium dioxide ($TiO_2$) can be in the anatase form. As recognized by those skilled in the catalytic art, the titania support material needs to be judiciously evaluated since certain grades may have impurities that interfere with the catalytic activity. Normally, with recognition of the previous caveat, the titanium dioxide may be prepared by any conventional technique. The titanium dioxide used in the catalyst of this invention may be composed of substantially porous particles of a diameter of from about 0.4 to about 0.7 micron and preferably has a specific surface area of at least about 1 $m^2/g$.

The metal oxide supported catalysts of this invention may be prepared by impregnation techniques well-known in the art, such as incipient wetness, grafting, equilibrium adsorption, vapor deposition, thermal spreading, and the like. When using an incipient wetness impregnation technique, an aqueous or nonaqueous solution containing a metal oxide precursor compound is contacted with the metal oxide support or substrate material, such as titania, for a time sufficient to deposit a metal oxide precursor material onto the support such as by selective adsorption or alternatively, excess solvent may be evaporated leaving behind the precursor compound or salt. If an incipient wetness impregnation technique is used to prepare a catalyst of this invention, the metal oxide precursor (such as a salt) solution used may be aqueous or organic, the only requirement being that an adequate amount of a precursor compound for the selected metal oxide be soluble in the solvent used in preparing this solution. Other impregnation techniques, such as vapor deposition and thermal spreading, do not require use of a solvent as does incipient wetness, and may be desirable in some circumstances to avoid the problem of volatile organic carbon (VOC) emissions.

For example, one way to disperse vanadium oxide, tungsten oxide, or a combination of the two oxides onto a titania metal oxide support or substrate is to impregnate titania spheres or powder (spheres or powder are used as representative examples of shapes of titania) with a solution containing a vanadium or a tungsten compound. When impregnating a substrate with both oxides, the tungsten and vanadium are introduced in a stepwise manner, tungsten first, followed by vanadium, with appropriate intermediate drying and calcining steps. Each solution may be an aqueous solution, one using an organic solvent, or a mixture of the two. Generally, an aqueous solution is preferred. Criteria used to choose the vanadium and tungsten compounds include whether the compounds are soluble in the desired solvent and whether the compounds decompose at an acceptable rate at a high calcination temperature to give the appropriate metal oxide. Illustrative of suitable compounds of vanadium and tungsten are the halides of vanadium and tungsten, oxyacids, oxyacid salts, and oxysalts of vanadium and tungsten. Specific examples are tungsten dibromide, tungsten pentabromide, tungsten tetrachloride, tungsten dioxydichloride, tungstic acid, ammonium meta-tungstate, vanadium tribromide, vanadium dichloride, vanadium trichloride, vanadium oxychloride, vanadium oxydichloride, vanadic acid, vanadyl sulfate, vanadium alkoxides, vanadium oxalate (which may be formed in situ by reaction of $V_2O_5$ and an aqueous solution of oxalic acid), and ammonium meta-vanadate. Suitable metal oxide precursor compounds for the other metal species suitable for making the supported metal oxide catalysts of this invention are well recognized by those skilled in the catalysis art.

The impregnation of the metal oxide support or substrate, such as titania support spheres or powder, with the metal oxide precursor compound solution may be carried out, as noted above, in ways well known in the art using either wet or dry impregnation techniques. One convenient method is to place the metal oxide support or substrate, e.g., titania particles, into a rotary evaporator which is equipped with a steam jacket. An impregnating solution of a precursor compound which contains an amount of the desired metal to be included in the finished catalyst (as the metal) is added to the support particles and the mixture is cold rolled (no steam) for a time, from about 10 to 60 minutes, sufficient to impregnate the support with the precursor compound solution. Next, steam is introduced and the solvent is evaporated from the impregnated solution. This usually takes from about 1 to about 4 hours. The impregnated support normally will be dried at temperatures ranging from about 50°–300° C. to remove excess solvent.

Water-soluble precursor compounds are generally preferred for industrial applications because of the environmental concern about VOC emissions. Nonetheless, when using an organic solvent, initial heating may be done in a nitrogen atmosphere to remove any flammable solvent. Finally, the support particles are removed from the rotary evaporator and calcined in a suitable oxidizing atmosphere such as air, oxygen, etc. at a temperature of about 150° to 800° C., and more usually from 400°–600° C., preferably for about 1 to about 3 hours, sufficient to decompose the precursor compound to the corresponding metal oxide. In other cases, as recognized by those skilled in the art, calcining conditions need to be adjusted to avoid undesirably reducing surface area.

Because some precursor compounds are air/moisture sensitive, they are prepared under a nitrogen atmosphere, as is recognized by those skilled in this art. The time required to calcine the composite will, of course, depend on the temperature and, in general, will range from about 0.5–7 hours. Calcination at 450° C. for about 2 hours has proven to be suitable for 1% vanadia on titania catalyst. The precise time and temperature for calcination depends on the particular metal oxide overlayer and should be selected to avoid adversely affecting the metal oxide support, e.g., in the case of a titania metal oxide support, to avoid substantial crystal phase transformation of the anatase into another crystalline form, such as rutile. Reducing atmospheres may also be used to decompose the transition metal oxide precursors, but the resulting composite will then require subsequent calcination to convert the reduced metal component to the oxide form. If the support is to be provided with an overlayer of a combination of metal oxides, e.g., if an overlayer containing both vanadium and tungsten oxide is desired, then the metal oxide precursor compounds may be impregnated on the metal oxide support simultaneously, but preferably are impregnated sequentially as previously noted.

The metal oxide supported catalysts of this invention will generally have surface metal oxide loadings of from about 0.5 to 35 wt. % metal oxide based on the total active catalyst composition, preferably from about 1 to 20 wt. %, more usually from about 1–15 wt. %, and most preferably 1–10 wt. % based on the total active catalyst composition.

While titania, silica, zirconia, alumina, niobia, ceria, magnesia, lanthanum oxide and tin oxide are conveniently referred to as supports or substrates in the description of the preferred embodiment of the present invention, based to a large degree on the way the catalyst is prepared, it should be noted that they provide important roles as active catalytic components in the supported metal oxide catalyst. Combination supports may also be advantageous. For example, substrates constituting a mixture of titania and zirconia or titania and silica can be used.

Further details on the preparation and structure of such metal oxide supported catalysts useful in the practice of the present invention can be found in Jehng et al., *Applied Catalysis A*, 83, (1992) 179–200; Kim and Wachs, *Journal of Catalysis*, 142, 166–171; Jehng and Wachs, *Catalysis Today*, 16, (1993) 417–426; Kim and Wachs, *Journal of*

Catalysis, 141, (1993) 419–429; Deo et al., Applied Catalysis A, 91, (1992) 27–42; Deo and Wachs, Journal of Catalysis, 146, (1994) 323–334; Deo and Wachs, Journal of Catalysis, 146, (1994) 335–345; Jehng et al., J Chem. Soc. Faraday Trans., 91(5), (1995) 953–961; Kim et al., Journal of Catalysis, 146, (1994) 268–277; Banares et al., Journal of Catalysis, 150, (1994) 407–420 and Jehng and Wachs, Catalyst Letters, 13, (1992) 9–20, the disclosure of which are incorporated herein by reference.

Preferred supported metal oxide catalysts are those which are known to be suitable for converting methanol to formaldehyde. Particularly preferred are supported metal oxide catalysts comprising a vanadia overlayer on a titania support.

It often is desired that the metal oxide, such as titania, silica, zirconia, alumina niobia, magnesia, ceria, lanthanum oxide, tin oxide, and their mixtures, used as a catalyst support component in accordance with the present invention have a surface area in the range of about 10 to about 150 $m^2/g$ and higher. These materials may be used in any configuration, shape, or size that exposes their surface and any metal oxide layer dispersed thereon to the gaseous stream passed in contact therewith. For example, these oxide supports, such as titania conveniently can be employed in a particulate form or deposited (before or after impregnation with the metal oxide overlayer) on a monolithic carrier or onto ceramic rings or pellets. As particles, the support, such as titania, can be formed in the shape of pills, pellets, granules, rings, spheres and the like. Use of free particulates might be desirable when large catalyst volumes are needed or if the catalyst bed is operated in a fluidized state. A monolithic form or deposition of the active catalyst on an inert ceramic support might be preferred in applications where catalyst movement is to be avoided because of concerns about catalyst attrition and dusting, and a possible increase in pressure drop across a particulate bed. In a preferred approach, a metal oxide supported catalyst, such as a vanadia on titania catalyst, may be deposited on a ceramic carrier such as silicon carbide, silicon nitride, carborundum stealite, alumina and the like, provided in the shape of rings or pellets. Typically, the active catalyst will be applied to the inert ceramic support in an amount to provide 1 to 10% by weight of the supported catalyst.

As noted, the present invention also contemplates the use of bulk metal oxides as the catalyst for converting methyl mercaptan to formaldehyde. Such bulk metal oxide catalysts generally constitute molybdates (Mo), chromates (Cr), vanadates (V), rhenates (Re), titinates (Ti), niobates (Nb), tungstates (W), manganates (Mn) and mixtures thereof. Such metal oxides also contain a wide variety of other metal species such as alkali metals (such as sodium (Na), lithium (Li), potassium (K) and cesium (Cs)), alklaine earth metals (such as calcium (Ca), barium (Ba), and magnesium (Mg)) and transition metals (such as copper (Cu), nickel (Ni), cobalt (Co), aluminum (Al), lead (Pb), bismuth (Bi), iron (Fe), zinc (Zn), cadmium (Cd), tellurium (Te), manganese (Mn)). Those skilled in the art recognize the wide variety of available bulk metal oxide catalysts. As a general rule, those bulk metal oxide catalysts known to be suitable for converting methanol to formaldehyde also may be suitable for the methyl mercaptan to formaldehyde conversion of the present invention.

Methods for making bulk metal oxide catalysts used in the present invention also are well known to those skilled in the art. In particular, the active catalyst can be prepared by physically blending the metal oxides, by coprecipitation from aqueous solutions containing soluble compounds of the catalyst components in the desired molar ratio, or by any other technique that provides an intimate mixture of the metal oxide constituents. For example, an aqueous solution of a water-soluble molybdenum compound (ammonium heptamolybdate) is mixed with a water-soluble iron compound (ferric chloride) to cause coprecipitation of both molybdenum and iron, using procedures well known to those skilled in the art. The coprecipitate is washed to eliminate the soluble salts formed during the coprecipitation reactions, filtered, dried, and calcined to convert the metal constituents to their active iron molybdate (oxide) form. Those skilled in the art recognize a variety of water soluble metal compounds that can be used to prepare the active catalyst. Alternatively, oxides of the respective metals may be ground together and calcined. Additional details on bulk metal oxides and bulk metal oxide catalysis can be found in Arora et al., Journals of Catalysis, 159, (1996) 1–13, which is incorporated herein by reference.

Those skilled in the art recognize that there exists a wide range of compounds, generally used in admixture, suitable for preparing bulk metal oxide catalysts. The following is a representative, though not exhaustive, list of possible constituents: bulk vanadates such as $PbV_2O_6$, $NaVO_3$, $Na_3VO_4$, $BiVO_4$ and other Bi-V-O family members, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$ and other V-P-O family members, $KVO_3$, $Pb_2V_2O_7$, and $TlVO_4$; bulk molybdates such as $PbMoO_4$, $CaMoO_4$, $Bi_2Mo_2O_9$, $Bi_3(FeO_4)(MoO_4)_3$ and other Bi-Mo-O family members, $Na_2MoO_4$, $MnMoO_4$, $Gd_2(MoO_4)_3$, $MgMoO_4$, $CuMoO_4$, $CoMoO_4$, $ZnMoO_4$, $Ce(MoO_4)_2$, $Ni_{0.5}Co_{0.5}MoO_4$, $Fe_2(MoO_4)_3$, $Te_2MoO_7$, $CoMoO_4$, $Al_2(MoO_4)_3$, $Cr_2(MoO_4)_3$, and $Na_2Mo_2O_7$; bulk niobates such as $YNbO_4$, $YbNbO_4$, $LiNbO_3$, $NaNbO_3$, $KNbO_3$, $AlNbO_4$, $K_8Nb_6O_{19}$, $BiNbO_4$, and other Bi-Nb-O family members, $SbNbO_4$, $NbOPO_4$, $CaNb_2O_6$, $K_4Nb_6O_{17}$, and $KCa_2Nb_3O_{10}$; bulk tungstates such as $Li_6WO_6$, $FeWO_4$, $CoWO_4$, $MnWO_4$, $NiWO_4$, $CuWO_4$, $CaWO_4$, $Cs_2WO_4$, $Na_2WO_4$, $B_aWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, and other Bi-W-O family members; bulk chromates such as $Na_2CrO_4$, $Na_2Cr_2O_7$, $Na_2Cr_3O_{10}$, $Na_2Cr_4O_{13}$, $K_2CrO_4$, $K_2Cr_2O_7$, $K_2Cr_3O_{10}$, $K_2Cr_4O_{13}$, $Fe_2(CrO_4)_3$, $CaCrO_4$, $Cs_2CrO_4$, $BiCrO_4$ and other Bi-Cr-O family members; bulk rhenates such as $NaReO_4$, $Li_6ReO_4$, and $Mg(ReO_4)_2$; bulk titanates such as $Na_2TiO_4$, $NaTiO_3$, $BaTiO_4$, $BaTiO_3$, and other Ba-Ti-O family members and bulk manganates such as $MnAl_2O_4$, $KMnO_4$, $MnO$, $MnO_2$, $Mn_2O_3$, $Mn_3O_4$. Further, information may be found in J. Raman Spectroscopy, 21, 683–691 (1990); J. Physical Chemistry, 95(13), 5031–5041 (1991); Solid State Ionics, 45, 201–213 (1991); J. Raman Spectroscopy, 26, 397–405 (1995); and J. Chem., Soc., Faraday Trans., 92(11), 1969–1973 (1996), all of which are incorporated herein by reference.

EXAMPLES

To facilitate a more complete understanding of the invention, a number of Examples are provided below. The scope of the invention, however, is not limited to specific embodiments disclosed in these Examples, which are for purposes of illustration only.

Catalyst Preparation and Characterization

Supported metal oxide catalysts were prepared as follows:

PREPARATION EXAMPLE 1: VANADIA ON TITANIA

A vanadia on titania metal oxide supported catalyst was prepared in accordance with the following procedure. The vanadia-titania catalyst was prepared by using $TiO_2$ (Degussa P25) as the support. The $TiO_2$ support (~10% rutile and ~90% anatase) possessed a surface area of ~55 $m^2/g$. It was calcined in air at 500° C. and cooled to room temperature before impregnation with the vanadium oxide precursor. The vanadium oxide overlayers on the $TiO_2$ support were prepared from vanadium triisopropoxide oxide (Alfa, 95–98% purity) by the incipient wetness impregnation method. The preparation was performed under a nitrogen environment and in nonaqueous solutions, since the alkoxide precursor is air and moisture sensitive. Solutions of known amounts of vanadium triisopropoxide oxide and propanol-2, corresponding to the incipient wetness impregnation volume and the final amount of vanadium required, were prepared in a glove box filled with nitrogen. The solutions of the vanadium precursor and propanol-2 were then thoroughly mixed with the titania support and dried at room temperature in the glove box for 24 hr. The impregnated samples were heated to 300° C. in flowing nitrogen and the final calcination was performed in $O_2$ (Linde, 99.9% pure) at 500° C. for 15 hours. The catalyst was then pelletized, crushed and sieved to obtain catalyst particles sizes between 100 to 200 µm.

PREPARATION EXAMPLE 1A: VANADIA ON TITANIA

Another vanadia on titania metal oxide supported catalyst was prepared using the general procedure of Preparation Example 1 except that the final calcination was conducted at 450° C. for 2 hours.

PREPARATION EXAMPLE 2: MOLYBDENUM OXIDE ON TITANIA

An aqueous solution of ammonium heptamolybdate $((NH_4)_6Mo_7O_{24}.4H_2O)$ (Alfa) was deposited onto $TiO_2$ (Degussa P25) as the support (~10% rutile and ~90% anatase) by the incipient wetness technique. As in Example 1, the support was calcined in air at 500° C. and cooled to room temperature before impregnation with the molybdenum oxide precursor. The support possessed a surface area of ~55 $m^2/g$. After impregnation, the wet samples were dried at room temperature for 16 hours, further dried at 110–120° C. for 16 hours, and calcined at 450° C. for 12 hours. The catalyst was then pelletized, crushed and sieved to obtain catalyst particles sizes between 100 to 200 µm.

PREPARATION EXAMPLE 3: CHROMIA ON TITANIA

An aqueous solution of chromium nitrate $(Cr(NO_3)_3.9H_2O)$ (Allied Chemical Co.) was deposited onto $TiO_2$ (Degussa P25) as the support using the incipient wetness technique. As in the previous Examples, the $TiO_2$ support (~10% rutile and ~90% anatase) was calcined in air at 500° C. and cooled to room temperature before impregnation with the chromium precursor. The support possessed a surface area of ~55 $m^2/g$. After impregnation, the wet samples were dried at room temperature for 16 hours, further dried at 110–120° C. for 16 hours, and calcined at 450° C. for 13 hours. The catalyst was then pelletized, crushed and sieved to obtain catalyst particles sizes between 100 to 200 µm.

PREPARATION EXAMPLE 4: RHENIUM OXIDE ON TITANIA

An aqueous solution of perrhenic acid $(HReO_4)$ (Aldrich) was deposited onto $TiO_2$ (Degussa P25) as the support using the incipient wetness technique. As before, the $TiO_2$ support (~10% rutile and ~90% anatase) was calcined in air at 500° C. and cooled to room temperature before impregnation with the rhenium oxide precursor. The support possessed a surface area of ~55 $m^2/g$. After impregnation, the wet samples were dried at room temperature for 16 hours, further dried at 110–120° C. for 16 hours, and calcined at 450° C. for 13 hours. The catalyst was then pelletized, crushed and sieved to obtain catalyst particles sizes between 100 to 200 µm.

PREPARATION EXAMPLE 5: VANADIA ON ZIRCONIA

A vanadium oxide overlayer was deposited onto a zirconium oxide $(ZrO_2)$ support (Degussa) having a surface area ~39 $m^2/g$ using an organic solution of vanadium triisopropoxide oxide (Alfa, 95–98% purity). In particular, the vanadium overlayer was prepared by the incipient wetness impregnation method using a solution of vanadium triisopropoxide oxide and propanol-2 in a glove box filled with nitrogen. The solutions of the vanadium precursor and propanol-2 were thoroughly mixed with the zirconia support and dried at room temperature for 16 hours, further dried at 110–120° C. for 16 hours, and calcined at 450° C. for 16 hours. The catalyst was then pelletized, crushed and sieved to obtain catalyst particles sizes between 100 to 200 µm.

PREPARATION EXAMPLE 6: VANADIA ON NIOBIA

A vanadium oxide overlayer was deposited on a niobia $(Nb_2O_5)$ support (55 $m^2/g$) using vanadium triisopropoxide oxide (Alfa, 95–98% purity) and the incipient wetness technique. The niobia support was prepared by calcining niobic acid (Niobia Products Co.) at 500° C. for two hours. A solution of vanadium triisopropoxide oxide and propanol-2 was thoroughly mixed with the niobia support in a glove box filled with nitrogen, dried at room temperature for 16 hours, further dried at 110–120° C. for 16 hours, and calcined at 450° C. for 16 hours. The catalyst was then pelletized, crushed, and sieved to obtain catalyst particles sizes between 100 to 200 µm.

PREPARATION EXAMPLE 7: VANADIA ON ALUMINA

A vanadium oxide overlayer was deposited on an alumina $(Al_2O_3)$ support (Harshaw, 180 $m^2/g$) using an organic solution of vanadium triisopropoxide oxide (Alfa, 95–98% purity) and the incipient wetness impregnation. A solution of the vanadium precursor and propanol-2 was thoroughly mixed with the alumina support, in a glove box filled with nitrogen, dried at room temperature for 16 hours, further dried at 110–120° C. for 16 hours, and calcined at 500° C. for 16 hours. The catalyst was then pelletized, crushed, and sieved to obtain catalyst particles sizes between 100 to 200 µm.

PREPARATION EXAMPLE 8: VANADIA ON SILICA

A vanadium oxide overlayer was deposited on a silica $(SiO_2)$ support (Cab-O-Sil, 300 $m^2/g$) using an organic solution of vanadium triisopropoxide oxide (Alfa, 95–98% purity) and the incipient wetness impregnation. A solution of the vanadium precursor and propanol-2 was thoroughly mixed, in a glove box filled with nitrogen with the $SiO_2$ support,. The wet silica was dried at room temperature for 16 hours, further dried at 110–120° C. for 16 hours, and calcined at 500° C. for 16 hours. The catalyst was then pelletized, crushed, and sieved to obtain catalyst particles sizes between 100 to 200 μm.

PREPARATION EXAMPLE 9: TUNGSTEN OXIDE ON SILICA

An aqueous solution of ammonium metatungstate $((NH_4)_6 H_2W_{12}O_{40} \cdot xH_2O)$ (Pfaltz & Bauer, 99.9% purity) was deposited as an oxide overlayer onto a silica $(SiO_2)$ support (Cab-O-Sil, 300 m$^2$/g) using the incipient wetness technique. After impregnation, the silica support was dried at room temperature for 16 hours, further dried at 110–120° C. for 16 hours, and calcined at 500° C. for 16 hours. The catalyst was then pelletized, crushed, and sieved to obtain catalyst particles sizes between 100 to 200 μm.

PREPARATION EXAMPLE 10: NIOBIA ON SILICA

An aqueous solution of niobium oxalate (Niobium Products Co.) was deposited onto a silica $(SiO_2)$ support (Cab-O-Sil, 300 m$^2$/g) using the incipient wetness technique. After impregnation, the silica support was dried at room temperature for 16 hours, further dried at 110–120° C. for 16 hours, and calcined at 500° C. for 16 hours. The catalyst was then pelletized, crushed, and sieved to obtain catalyst particles sizes between 100 to 200 μm.

PREPARATION EXAMPLE 11: TITANIA ON SILICA

Titanium isopropoxide (Aldrich) in a toluene solution was impregnated onto a silica $(SiO_2)$ support (Cab-O-Sil, 300 m$^2$/g) under a nitrogen blanket to form a titania overlayer using the incipient wetness technique. After impregnation, the wet silica was dried at room temperature for 16 hours, further dried at 110–120° C. for 16 hours, and calcined at 500° C. for 16 hours. The catalyst was then pelletized, crushed, and sieved to obtain catalyst particles sizes between 100 to 200 μm.

PREPARATION EXAMPLE 12: VANADIA AND TUNGSTEN OXIDE ON TITAMA

A vanadia and tungsten oxide on titania catalyst was prepared by a two step incipient wetness impregnation method. A vanadium oxide overlayer was deposited first on the $TiO_2$ support using a solution of vanadium triisopropoxide oxide (Alfa, 95–98% purity) and propanol-2 by the incipient wetness impregnation method in a glove box filled with nitrogen. The solution of the vanadium precursor and propanol-2 were thoroughly mixed with the $TiO_2$ (Degussa P25) as the support. The $TiO_2$ support (~10% rutile and ~90% anatase) was prepared by previous calcination in air at 500° C. and cooled to room temperature before impregnation with the vanadium oxide precursor. The support possessed a surface area of ~55 m$^2$/g. After impregnation, the wet $TiO_2$ was dried at room temperature for 16 hours, further dried at 110–120° C. for 16 hours, and calcined at 450° C. for 12 hours. Subsequently, an aqueous solution of ammonium metatungstate $((NH_4)_6H_2W_{12}O_{40} \cdot xH_2O)$ was deposited as an oxide overlayer onto the $TiO_2$ support, again using the incipient wetness technique. After impregnation, the wet samples were dried at room temperature for 16 hours, further dried at 110–120° C. for 16 hours, and calcined at 500° C. for 16 hours. The catalyst was then pelletized, crushed, and sieved to obtain catalyst particles sizes between 100 to 200 μm.

PREPARATION EXAMPLE 13: VANADIA AND TITANIA ON SILICA

A vanadia and titania on silica catalyst was prepared by a two-step incipient wetness impregnation method. The silica support used for this study was Cabosil EH-5 (380 m$^2$/g). This fluffy material was treated with water to condense its volume for easier handling. Then the wet SiO2 was dried at 120° C. and subsequently calcined at 500° C. overnight. The resulting surface area was 332 m$^2$/g. This water pretreatment did not change the dispersion ability of the silica, because an isopropanol pretreated silica also resulted in the same surface area and the same dispersion capacity. A titanium oxide overlayer was deposited first on the silica $(SiO_2)$ support under a nitrogen blanket using titanium isopropoxide (Aldrich) in a toluene solution by the incipient wetness impregnation method in a glove box filled with nitrogen. After impregnation, the loaded sample was dried at room temperature for 16 hours, further dried at 110–120° C. for 16 hours, and calcined at 500° C. for 4 hours. Subsequently, a solution of vanadium triisopropoxide oxide (Alfa, 95–98% purity) and propanol-2 was impregnated onto the silica $(SiO_2)$ support containing titania, again using the incipient wetness technique. The solution of the vanadium precursor and propanol-2 was thoroughly mixed with the $SiO_2$ support containing titania. After impregnation, the wet $SiO_2$ was dried at room temperature for 16 hours, further dried at 110–120° C. for 16 hours, and calcined at 450° C. for 2 hours. The catalyst was then pelletized, crushed and sieved to obtain catalyst particles sizes between 100 to 200 μm.

The above-synthesized catalysts, as well as one other bulk metal oxide catalyst, were examined for their ability to oxidize methyl mercaptans selectively to formaldehyde generally using the following equipment and methods.

Catalytic Reactor

The oxidation reactions were carried out in an isothermal fixed-bed integral mode reactor operating at atmospheric pressure. The methanethiol ($CH_3SH$), diluted in helium, was supplied by Scott Specialty Gases. The reactant gas was further diluted in helium and air (Blue Valley Welding Supply, total hydrocarbons concentration >1 ppm, $H_2O$ concentration >3 ppm) and sent to the reactor through glass tubing connected with Teflon fittings. Flow rates and concentrations were controlled by two mass flow controllers (Brooks 5850 D, 1-100 sccm for helium and Omega FMA-767-V, 0-1 slpm for the reactants). The lines were heated to 70° C. for the methanethiol oxidation studies to prevent condensation. The total gas flow was maintained between 150 and 200 ml/min. The reactor was kept in a vertical position and made of 6-mm O.D. Pyrex glass. Heating tape was used in conjunction with a feedback temperature controller (Omega CN 9000) to obtain the desired reactor temperature. The catalysts were held at the middle of the reactor tube between a porous glass frit, pore size of 40 to 60 μm, and a glass wool plug. Each catalyst sample was always pretreated by heating at 500° C. for 2 to 3 hours in flowing air to remove adsorbed water on the catalyst surface prior to initiation of an experiment. The outlet of the reactor was connected to an FTIR cell (Infrared Analysis, Inc; Model #G-4-Tin-Ta-Ba-Ag), that was used to analyze the reaction products. The lines between the outlet and the cell were heated to avoid condensation of the products. The flow rate of reaction products sent to the FTIR cell was controlled by a needle valve (Nupro Company, SS-4BRG).

Composition Analysis by FTIR

Analysis of the reaction products was accomplished using a Midac Inc. FTIR, (Model #101250, series 2–4). Samples were analyzed in a path gas cell (Infrared Analysis, Inc;

Model #G-4-Tin-Ta-Ba-Ag), that has an effective length of 10 m and a volume of 3.1 L. The spectrometer was controlled by a microcomputer (Sprouse Scientific, model TECH- 1000A) to provide acquisition and manipulation of the spectra: display, subtraction, zoom, etc. The spectra were obtained using 16 scans at a resolution of 0.5 cm$^{-1}$. The FTIR analysis required about 10 minutes.

Methanethiol oxidation was investigated with a variety of supported metal oxide and bulk metal oxide catalysts as follows:

EXAMPLE 1

In a series of experiments, a supported oxide catalyst prepared in accordance with Preparation Example 1, comprising about 1% vanadia ($V_2O_5$) on titania ($TiO_2$) catalyst, was contacted with a nitrogen stream containing methanethiol over a wide temperature range to optimize the formation of formaldehyde. Mercaptan conversions were measured by both increasing and decreasing the temperature between 200 and 450° C., and no temperature hysteresis was observed. The exit concentration of the reaction products of this methanethiol oxidation over the 1% $V_2O/TiO_2$ catalyst as a function of temperature is graphically presented in FIG. 1. As illustrated, formaldehyde was found to be the predominant product. In these tests, dimethylthiomethane ($H_2C(SCH_3)_2$) was observed as an intermediate between 200 to 300° C., and dimethyl disulfide ($CH_3S)_2$ was found as an intermediate between 300 to 400° K. Carbon monoxide (CO) and carbon dioxide appeared in small amounts as reaction products; the formation of CO increased at elevated temperatures. Sulfur dioxide production tracked the formation of formaldehyde.

Figure 2:
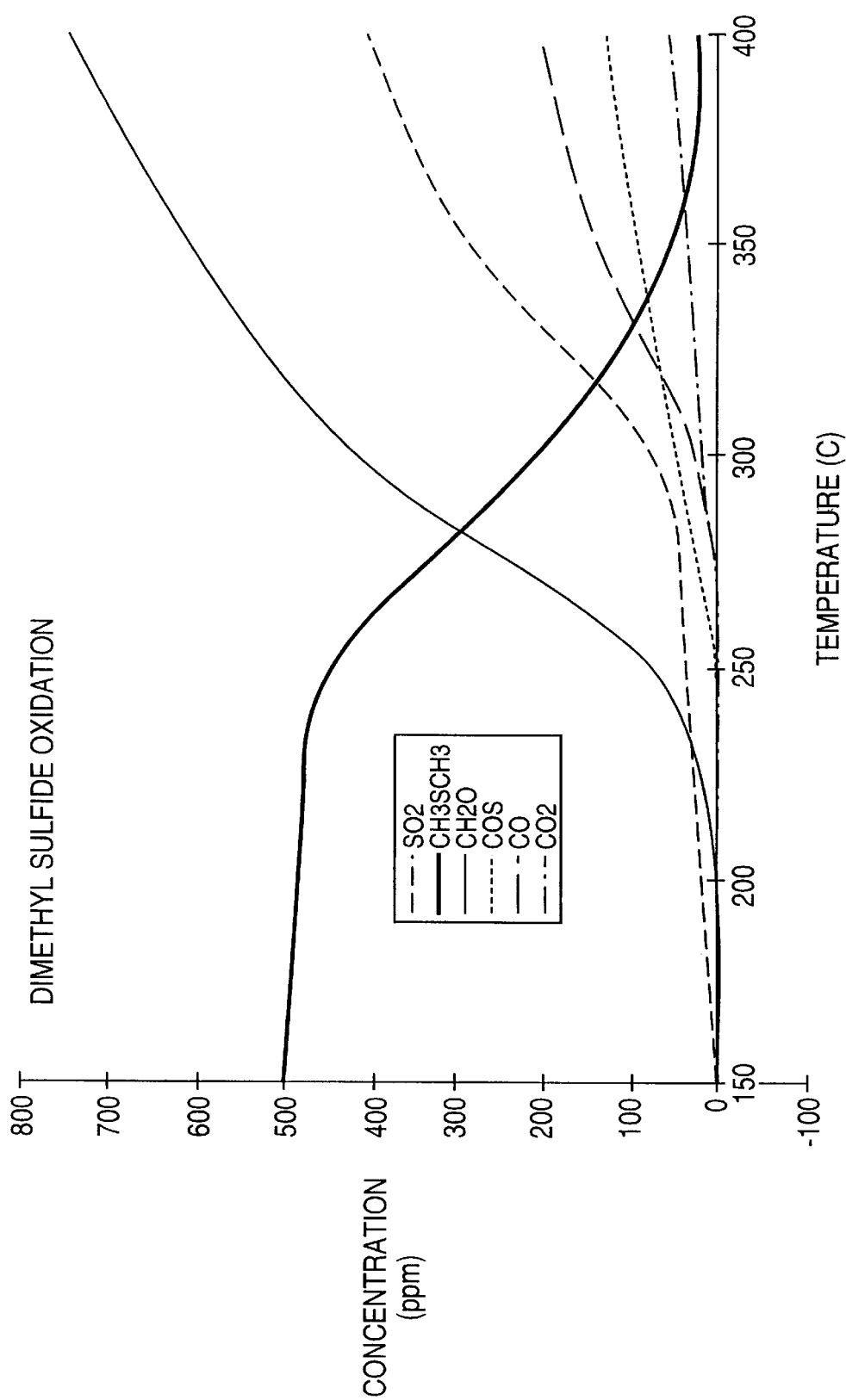
FIG. 2 illustrates the distribution of products (exit concentration of reactor) produced by oxidizing dimethyl sulfide over a vanadia on titania catalyst containing about 1% by weight vanadia over the temperature range of 150° to 400° C.
Figure 3:
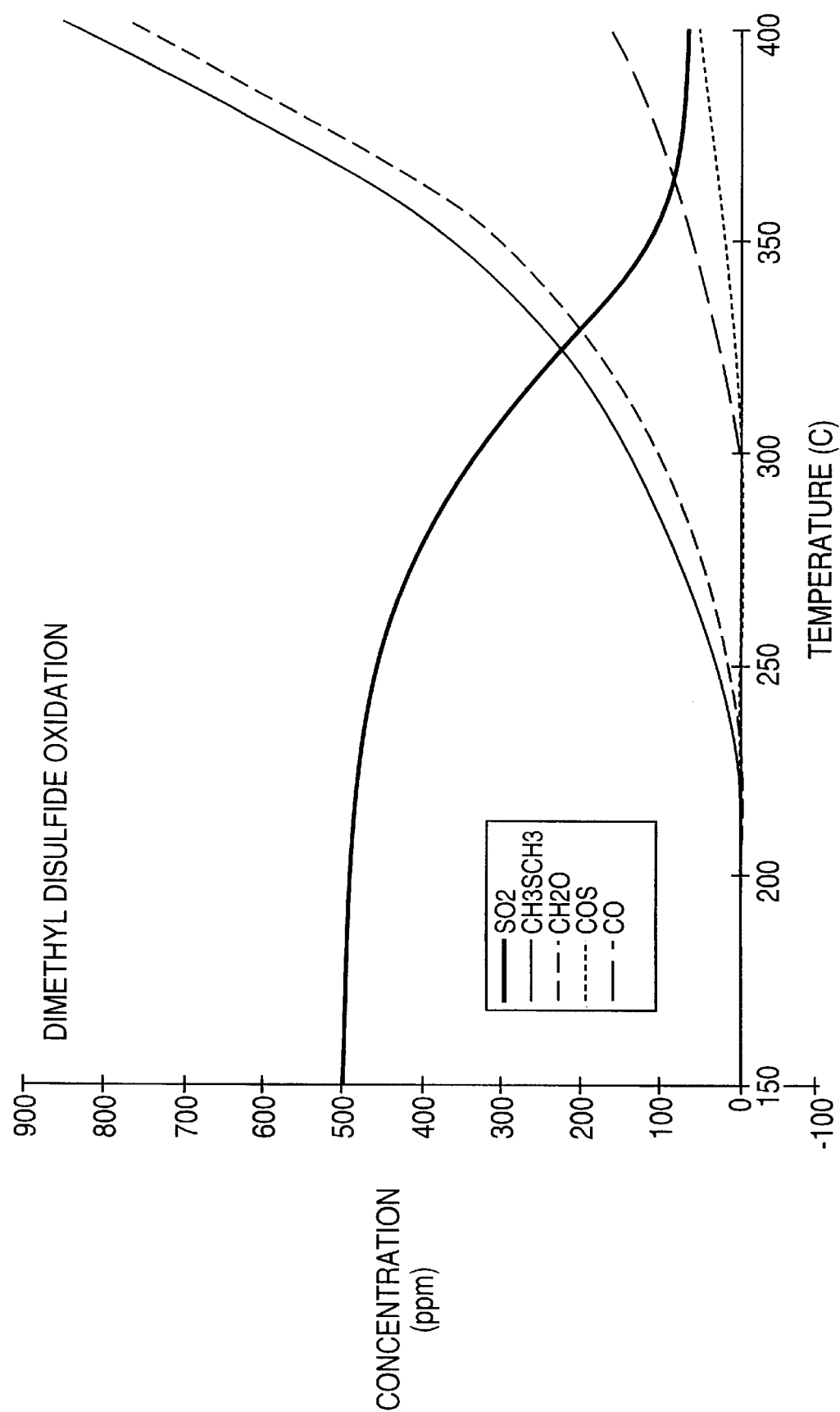
FIG. 3 illustrates the distribution of products (exit concentration of reactor) produced by oxidizing dimethyl disulfide over a vanadia on titania catalyst containing about 1% by weight vanadia over the temperature range of 150° to 450° C.

The same equipment and procedures were used to examine the behavior of dimethyl sulfide and dimethyl disulfide over the same catalyst and a similar temperature range. The results are shown in FIGS. 2 and 3.

EXAMPLES 2–16

Using substantially the same equipment and procedures as Example 1, a variety of both metal oxide supported catalysts and a bulk metal oxide catalyst were tested for their ability to oxidize methanethiol selectively to formaldehyde. While the majority of the data were obtained at a reaction temperature of 350° C., Examples 8, and 12–14 were run at 400° C., because formaldehyde was not detected in the product using these catalysts at 350° C. The feed gas contained 1150 ppm of methanethiol and was introduced into the reactor at a volumetric flow rate of 150 ml/min. The ironmolybdate catalyst contained iron ($Fe_2O_3$) and molybdenum ($MoO_3$) in a molar ratio (Fe:Mo) of 1.0/2.15 and was obtained from Perstorp. The results of these tests are reported in Table 1.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

TABLE 1

| Example | Catalyst | Preparation Example | Catalyst Load (mg) | Conversion of $CH_3SH$ (Mole %) | Selectivity (mol %) | | | |
|---|---|---|---|---|---|---|---|---|
| | | | | | Formaldehyde | Carbon Monoxide | Carbon Dioxide | COS |
| 2 | 1.15% $V_2O_5/TiO_2$ | 1 | 10 | 54 | 78 | 11 | 3 | 8 |
| 3 | 1% $V_2O_5/TiO_2$ | 1A | 10 | 48 | 84 | 10 | 4 | 2 |
| 4 | 1% $MoO_3/TiO_2$ | 2 | 100 | 84 | 79 | 12 | 9 | 0 |
| 5 | 1% $CrO_3/TiO_2$ | 3 | 100 | 79 | 81 | 12 | 7 | 0 |
| 6 | 1% $Re_2O_7/TiO_2$ | 4 | 10 | 80 | 76 | 18 | 3 | 2 |
| 7 | $Fe_2(MoO_4)_3 + MoO_3$ | — | 100 | 40 | 85 | 10 | 5 | 0 |
| 8 | 1% $V_2O_5/ZrO_2$ | 5 | 10 | 57 | 89 | 8 | 2.6 | 0.4 |
| 9 | 1% $V_2O_5/Nb_2O_5$ | 6 | 20 | 45 | 72 | 21 | 7 | 0 |
| 10 | 1% $V_2O_5/Al_2O_3$ | 7 | 100 | 61 | 37 | 16 | 6 | 41 |
| 11 | 1% $V_2O_5/SiO_2$ | 8 | 100 | 63 | 84 | 9 | 7 | 0 |
| 12 | 1% $WO_3/SiO_2$ | 9 | 100 | 46 | 49 | 11 | 4 | 36 |
| 13 | 2.5% $Nb_2O_5/SiO_2$ | 10 | 100 | 42 | 50 | 13 | 2 | 35 |
| 14 | 10% $TiO_2/SiO_2$ | 11 | 100 | 45 | 65 | 16 | 3 | 16 |
| 15 | 1% $V_2O_5/7\% WO_3 TiO_2$ | 12 | 10 | 52 | 82 | 14 | 4 | 0 |
| 16 | 10% $V_2O_5/$ 15% $TiO_2/SiO_2$ | 13 | 100 | 71 | 85 | 8 | 7 | 0 |

What is claimed is:

1. A process for selectively converting methyl mercaptans to formaldehyde comprising contacting a gas containing a methyl mercaptan with a catalyst selected from a supported metal oxide catalyst and a bulk metal oxide catalyst under oxidizing conditions for a time sufficient to convert at least a portion of the methyl mercaptan to formaldehyde and sulfur dioxide, and recovering said formaldehyde.

2. The process of claim 1 wherein the supported metal oxide catalyst has a metal oxide overlayer of a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof.

3. The process of claim 2 wherein the supported metal oxide catalyst has a metal oxide support selected from the group consisting of titania, silica, zirconia, alumina, niobia, magnesia, ceria, lanthanum oxide, tin oxide and mixtures thereof.

4. The process of claim 3 wherein the metal oxide overlayer comprises 0.5 to 35 percent by weight of the supported metal oxide catalyst.

5. The process of claim 4 wherein the supported metal oxide catalyst is selected from the group consisting of a vanadia overlayer on a titania support, a molybdenum oxide overlayer on a titania support, a chromium oxide overlayer on a titania support, a rhenium oxide overlayer on a titania support, a vanadia overlayer on a zirconia support, a vanadia overlayer on a niobia support, a vanadia overlayer on an alumina support, a vanadia overlayer on a silica support, a tungsten oxide overlayer on a silica support, a niobia overlayer on a silica support, and a titania overlayer on a silica support.

6. The process of claim 5 wherein the supported metal oxide catalyst comprises a vanadia overlayer, in an amount of 1 to 10% by weight of said supported metal catalyst, on a titania support.

7. The process of claim 1 wherein the bulk metal oxide catalyst is selected from the group consisting of molybdates (Mo), chromates (Cr), vanadates (V), rhenates (Re), titinates (Ti), niobates (Nb), tungstates (W), manganates (Mn) and mixtures thereof.

8. The process of claim 7 wherein the bulk metal oxide catalyst comprises at least one member selected from the group consisting of $PbV_2O_6$, $NaVO_3$, $Na_3VO_4$, $BiVO_4$, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$, $KVO_3$, $Pb_2V_2O_7$, $TlVO_4$, $PbMoO_4$, $CaMoO_4$, $Bi_2Mo_2O_9$, $Bi_3(FeO_4)(MoO_4)_3$, $Na2MoO_4$, $MnMoO_4$, $Gd_2(MoO_4)_3$, $MgMoO_4$, $CuMoO_4$, $CoMoO_4$, $ZnMoO_4$, $Ce(MoO_4)_2$, $Ni_{0.5}Co_{0.5}MoO_4$, $Fe_2(MoO_4)_3$, $Te_2MoO_7$, $CoMoO_4$, $Al_2(MoO_4)_3$, $Cr_2(MoO_4)_3$, $Na_2Mo_2O_7$, $YNbO_4$, $YbNbO_4$, $LiNbO_3$, $NaNbO_3$, $KNbO_3$, $AlNbO_4$, $K_8Nb_6O_{19}$, $BiNbO_4$, $SbNbO_4$, $NbOPO_4$, $CaNb_2O_6$, $K_4Nb_6O_7$, $KCa_2Nb_3O_{10}$, $Li_6WO_6$, $FeWO_4$, $CoWO_4$, $MnWO_4$, $NiWO_4$, $CuWO_4$, $CaWO_4$, $Cs_2WO_4$, $NaWO_4$, $BaWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $MnAl_2O_4$, $KMnO_4$, $MnO$, $MnO_2$, $Mn_2O_3$, $Mn_{3O4}$, $Na_2CrO_4$, $Na_2Cr_2O_7$, $Na_2Cr_3O_{10}$, $Na_2Cr_4O_{13}$, $K_2CrO_4$, $K_2Cr_2O_7$, $K_2Cr_3O_{10}$, $K_2Cr_4O_{13}$, $Fe_2(CrO_4)_3$, $CaCrO_4$, $CsCrO_4$, $BiCrO_4$, $NaReO_4$, $Li_6ReO_4$, $Mg(ReO_4)_2$, $Na_2TiO_4$, $NaTiO_3$, $BaTiO_4$, and $BaTiO_3$.

9. The process of claim 1 wherein said contacting is conducted at a temperature between 200° and 700° C.

10. The process of claim 7 wherein said contacting is conducted at a temperature between 325° and 500° C.

11. The process of claim 8 wherein said gas containing said methyl mercaptan is contacted with said catalyst such that between $10^{-2}$ and $10^4$ cubic centimeters of methyl mercaptan contacts a gram of catalyst per minute.

12. The process of claim 9 wherein between 0.1 and 100 cubic centimeters of methyl mercaptan contact a gram of catalyst per minute.

13. The process of claim 1 wherein the methyl mercaptan is selected from $CH_3SH$, $CH_3SCH_3$, $CH_3SSCH_3$ and mixtures thereof.

14. The process of claim 3 wherein said contacting is conducted at a temperature between 200° and 700° C.

15. The process of claim 14 wherein said contacting is conducted at a temperature between 325° and 500° C.

16. The process of claim 15 wherein said gas containing said methyl mercaptan is contacted with said catalyst such that between $10^{-2}$ and $10^4$ cubic centimeters of methyl mercaptan contacts a gram of catalyst per minute.

17. The process of claim 16 wherein between 0.1 and 100 cubic cntimeters of methyl mercaptan contact a gram of catalyst per minute.

18. The process of claim 7 wherein the methyl mercaptan is selected from $CH_3SH$, $CH_3SCH_3$, $CH_3SSCH_3$ and mixtures thereof.

19. The process of claim 9 wherein said contacting is conducted at a temperature between 325° and 500° C.

20. The process of claim 10 wherein between 0.1 and 100 cubic certimeters of methyl mercaptan contact a gram of catalyst per minute.

* * * * *

UNITED STATES PATENT AND TRADEMARK OFFICE
CERTIFICATE OF CORRECTION

PATENT NO.: 5,969,191

DATED: October 19, 1999

INVENTOR(S): Israel E. WACHS

It is certified that an error appears in the above-identified patent and that said Letters Patent is hereby corrected as shown below:

In claim 8, line 31:

After "$CsLuW_2O_8$," insert --$BiWO_4$--.

In claim 8, line 32:

Delete "$Mn_{3O4}$" and insert --$Mn_3O_4$--.

In claim 8, line 34:

Delete "$CsCrO4$" and insert --$Cs_2CrO_4$--.

Signed and Sealed this

Eleventh Day of April, 2000

Attest:

Q. TODD DICKINSON

Attesting Officer

Director of Patents and Trademarks